United States Patent
Trevisan

(10) Patent No.: US 6,365,170 B1
(45) Date of Patent: Apr. 2, 2002

(54) USE OF A DISINFECTANT FOR LIVING FISH

(75) Inventor: Augusto Trevisan, Verona (IT)

(73) Assignee: USF Filtration & Separations Spa-Div. Perdomini, Verona (IT)

(*) Notice: Subject to any disclaimer, the term of this patent is extended or adjusted under 35 U.S.C. 154(b) by 0 days.

(21) Appl. No.: 09/424,569

(22) PCT Filed: Dec. 16, 1998

(86) PCT No.: PCT/IT98/00366

§ 371 Date: Feb. 28, 2000

§ 102(e) Date: Feb. 28, 2000

(87) PCT Pub. No.: WO99/48362

PCT Pub. Date: Sep. 30, 1999

(30) Foreign Application Priority Data

Mar. 25, 1998 (IT) ........................................ VR98A0020

(51) Int. Cl.⁷ ................................................ A01N 25/02
(52) U.S. Cl. ...................... 424/406; 424/405; 424/616; 514/557; 119/215
(58) Field of Search ................................. 424/405, 406, 424/616; 514/557; 119/215

(56) References Cited

U.S. PATENT DOCUMENTS

| | | | |
|---|---|---|---|
| 5,313,911 A | | 5/1994 | Thomassen et al. |
| 5,393,781 A | | 2/1995 | Vegega et al. |
| 6,117,457 A | * | 9/2000 | Denos et al. ............... 424/616 |

FOREIGN PATENT DOCUMENTS

WO    WO 98/05311    2/1998

* cited by examiner

*Primary Examiner*—Neil S. Levy
(74) *Attorney, Agent, or Firm*—Oppenheimer, Wolff & Donnelly

(57) ABSTRACT

In a fish breeding facility, a disinfecting product is used which is suitable for eradicating microorganisms that affect fish fauna and that are present in said fish breeding facility; said disinfecting product comprises an aqueous solution of peracetic acid and hydrogen peroxide, wherein said peracetic acid is comprised in a percentage by weight ranging between 2% and 15% and said hydrogen peroxide is comprised in a percentage by weight ranging between 4% and 21%

8 Claims, No Drawings

USE OF A DISINFECTANT FOR LIVING FISH

FIELD OF THE INVENTION

The present invention relates to the use of a hydrogen peroxide and peracetic acid based disinfectant which is capable of eliminating parasite microorganisms that affect fish fauna, no matter whether it be in fresh or sea water.

The product according to the present invention is particularly suitable for the fish industry and in the fish growing field thereto related.

STATE OF THE ART

It is known that fish fauna, including heretofore both fresh water fish (such as eel, trout, and so on) and sea water fish (such as bass, dory, salmon, an so on), is often subject to the aggression of numerous microorganisms.

Infective and infestive pathology control on fish results to be extremely delicate and of paramount importance, mostly in the fish growing field, where considerable interests of economic nature are at stake.

It is known that some microorganisms find a dwelling and a source of nourishment inside the body of a fish, and, in order to be able to suppress said microorganisms, it is necessary to treat ill fish with specific antibiotics and chemiotherapeutics.

This means therefore that in order to obtain the eradication of these microorganisms, it is necessary to make fish undergo treatments with specific antibiotics administered in suitable doses.

On the other hand, if externally dwelling microorganisms are involved, these act and survive by attaching onto the hosting fish's skin, choosing particularly favorable sites of it, like for example near the tail or gills where they can objectively find a valid docking point and source of food for their survival.

Among said microorganisms are for example Ichthyophthirius sp., Tricodina sp., Costia sp., Mixobacteria, eel, trout and fresh water fish Saprolegna, "sea-lice" for sea water fish.

As these external microorganisms locate themselves on the skin of the fish that they find to be most suitable for them, their spreading amongst individuals belonging to the same group and/or environment results to be extremely simple and easy to occur, because of the frequent skin to skin contacts that do make it possible for the transfer of said external microorganisms to take place from an ill individual to a healthy one.

The technology currently employed for the suppression and/or detachment of said microorganisms involves the emplyment of disinfectants to be mixed with water in manners determined by whether environmental water has a low exchange rate, like for example that of a fish breeding plant, or a high one like that of a river, or that of a large or small volume of sea or of a lake basin.

In trout-growing for example, disinfectants are diluted in the water of the fish breeding plant so as to carry out both preventive and therapeutical treatments on adult fish and on their eggs in order to fight against particular forms of mycosis.

A particularly risky period is for example that of the pressing season because the handling and the stress from capture that fish are forced to undergo cause skin lesions on them together with the alteration of the protective phlegm present on their skin, thus favoring the occurrence of Saprolegnosis.

Among the disinfectants employed for parasite infestation control and against the external protozoans mentioned above, are for example formalin, copper sulphate, potassium permanganate, malachite green, chloramine T., sodium chloride, etcetera.

The main drawback of most of the disinfectants traditionally employed in order to suppress the microorganisms that affect fish fauna is represented by the fact that some of these are carcinogenic, and as such they are prohibited in compliance with the current special laws in force, or they are strongly suspected to be so.

A further more than slightly remarkable disadvantage of many disinfectants, such as for example formalin, is given by the environmental impact that they have because of their toxicity, mostly in areas where waste waters from fish growing farms are disposed of.

Many of such products are in fact not environmentally friendly and as a consequence of that there is the damage they cause on the natural environment where fish subjected to such treatments live, furthermore causing often irreparable damage to the flora and fauna present therein.

In so far as the employment of sodium chloride is concerned on the other hand, problems are essentially related to storage and transport of the product as very large amounts and volumes of it have to be used.

Furthermore it is known in the art that (reference is for example made to document U.S. Pat. No. 5,313,911) the employment of suitable concentrations of hydrogen peroxide as an antiparasite agent is advantageously viable against salmon louse (Lepeophtheirus Salmonis).

According to what disclosed in the above mentioned patent, hydrogen peroxide concentration is generally in the range between 1.2 and 5 g/l; moreover, that document discloses how it is possible to accomplish an optimum result, with a success percentage in the 100% range, and keeping hydrogen peroxide concentration around 1.5 g/l for a time lapse which is longer than 20 minutes.

The employment of peracetic acid is further known as a disinfectant which is traditionally employed for the disinfection of different types of premises and appliances.

For example, peracetic acid is advantageously employed in the zootechnic field for the disinfection of premises, fodder and bedsteads; in the agriculture and food fields for the disinfection of containers generally used in the beer, wine and milk and cheese industries; in the field of recycling and purifying water for human consumption; in the municipal and industrial waste liquid biological oxidation plants.

DESCRIPTION OF THE INVENTION

The present invention aims at overcoming the disadvantages and drawbacks of the prior art, and at proposing therefore a disinfecting product which is effective in suppressing and eradicating microorganisms that affect fish fauna, without nevertheless endangering the flora and fauna that dwell in the environment where said product is used.

The above aim has been accomplished by the features in the main claim.

Dependent claims outline particularly advantageous forms of embodiment of the present invention.

The disinfecting product employed in the present invention is an aqueous solution of peracetic acid and hydrogen peroxide, said product being used in a suitably diluted form so as to be effective in detaching and/or eradicating the above mentioned microorganisms, nonetheless without ever reaching concentrations that are proximal to the toxicity threshold that may endanger the life of the fish fauna treated and/or that may cause irreparable damages to the environment and/or the fauna or flora which have been treated.

According to the present invention, the disinfecting product comprises a percentage by weight of peracetic acid ranging between 2% and 15%, the hydrogen peroxide percentage corresponding to it being exactly proportional to the percentage of peracetic acid employed.

This means that the percentage by weight of hydrogen peroxide is generally in the range between 4% and 21%.

A preferred composition of the disinfecting product according to the present invention comprises a percentage of peracetic acid by weight equalling 5% and a corresponding percentage of hydrogen peroxide by weight equalling 20%.

In addition to hydrogen peroxide and peracetic acid, mentioned above, the disinfecting product employed in the present invention further comprises stabilizers and deionised water present in amounts needed to take up the mixture to 100%.

The stabilisers generally employed are those traditionally known to the skilled in the art, such as for example sulphuric acid.

According to the present invention, suitable doses of the product are used, for example in the range between 15 and 40 ppm.

Furthermore, according to the present invention the product is in the form of a clear and colorless solution, and the particular microbicide activity that characterises it is mainly due to some important properties of peracetic acid.

That acid in fact acts very rapidly, it is extremely effective even in the presence of large amounts of organic compounds, and it can be used at different temperatures; furthermore it does not give way to any residues, and finally it is a very strong oxidizing agent, this last feature being accountable for by the very much enhanced microbicide activity of the acid itself and of the product as a whole, too, particularly against viruses, numerous aerobic and anaerobic bacteria, molds, yeasts and fungi.

Said enhanced activity confers on the disinfecting product according to the present invention a remarkable interest of the specialized staff operating in the fish growing industry, most of all in case a drastic and extreme sanitation is necessary (known in the field as "stamping out") of the fish breeding plant and the equipment used for the definitive eradication of pathologies that may affect fish fauna grown in captivity.

Attention is indeed drawn to the fact that the EC norms presently in force are particularly strict as they impose the draining and drying out of the entire plant and its sanitation by disinfection of the water and equipment therein contained.

An extremely remarkable advantage given by using a disinfecting product according to the present invention is that said product is environmentally friendly, therefore it does not endanger the natural balance of the environment for which it is employed.

In fact, the hydrogen peroxide/peracetic acid mixture separates in water, oxygen and peracetic acid resulting both fully biodegradable and environmentally friendly.

Therefore this means that the disinfecting product according to the present invention does not cause the occurrence of pollution related problems at waste water disposal sites of fish breeding facilities, or in a portion of sea or lake, or in the stretch of a river where an antiparasitic treatment with the product according to the present invention has been or is being carried out.

Furthermore, the product according to the present invention is up to high enough safety standards at the handling and employment stages, as when it is applied, no fumes are produced that may be harmful to the workers.

Heretofore some examples of the employment made of predetermined amounts of the disinfecting product are given, with particular reference to some specific species of fish fauna affected by specific infective pathologies.

It should be given for granted that the cases that follow are taken in consideration exclusively by way of not limiting examples of the invention described in the present patent specification.

EXAMPLE I

In a fish breeding plant, 80% of the rainbow trouts therein contained result to be affected by Saprolegnosis.

The water in the fish breeding plant was kept at a temperature in the 6–70° C. range.

According to the present invention, in order to cope with the above mentioned pathology, said rainbow trouts are treated with a disinfecting product that comprises a percentage of peracetic acid equalling 5% and a corresponding percentage of hydrogen peroxide equalling 20%.

The treatment according to the present invention consists of letting a certain amount of disinfecting product drip into the water, said certain amount equalling to 25 ml/m$^3$, over a 45 minute time lapse.

The above described treatment is then repeated for 8 successive days and the result obtained is a remarkable suppression of the disease because, after that period of time, the percentage of rainbow trouts still affected by Saprolegnosis has dropped to 10%.

EXAMPLE II

Eighty per cent of the rainbow trouts in a fish breeding plant result to be affected by Saprolegnosis.

Water temperaure in the fish breeding facility is in the 6–7° C. range.

Following a similar procedure as that outlined in Example I, an amount of disinfecting product equalling 35 ml/m$^3$ is allowed to drip into the fish breeding facility over a 30 minute time lapse, and this is repeated for 8 successive days.

At the end of treatment the percentage of rainbow trouts that were still affected by Saprolegnosis is approx. 10%.

EXAMPLE III

In a fish breeding facility the eel population is affected by severe Tricodiniasis quantified by the presence of approx. 300 protozoans in each microscope field.

In the fish breeding facility, water is kept at a temperature of approx. 18° C.

According to what described in the previous examples, said eels are treated with a disinfecting product whose composition comprises a peracetic acid percentage equalling 5% and a corresponding hydrogen peroxide percentage equalling 20%.

The treatment according to the present invention consists of letting an amount of disinfecting product equalling 25 ml/m$^3$ drip into the water over a 4 hour period, said treatment being carried out every other day for a total of five treatments.

The result accomplished is a remarkable drop in the number of parasites from 300 to approx 10 units.

What is claimed is:

1. A method for destroying microorganisms existing on edible fish that affect edible fish farms and are present in an edible fish facility, said method including the step of pouring into the water of a fish facility a disinfecting product comprising an aqueous solution of peracetic acid and hydrogen peroxide, whereby peracetic acid comprises a percentage by weight ranging between 2% and 15% of the disinfecting product, hydrogen peroxide comprises a percentage by weight ranging between 4% and 21% of the disinfecting product, and the dosage range of the disinfecting product is between 15 and 40 ppm in the water of the fish facility.

2. The method according to claim 1 wherein said disinfecting product comprises peracetic acid with a percentage equalling 5 and hydrogen peroxide in a percentage equalling 20.

3. The method according to claim 1 wherein said disinfecting product comprises stabilisers and deionised water in amounts equalling those needed to take up the mixture to 100%.

4. The method according to claim 2, wherein said disinfecting product comprises stabilisers and deionised water in amounts equalling those needed to take up the mixture to 100%.

5. A method as claimed in claim 1 comprising adding the product at a rate of about 25 ml/m$^3$ of the water for a period of about 4 hours.

6. A method for destroying microorganisms that affect edible fish fauna and that are present in an artificially formed field for growing edible fish, said method including the step of pouring into the water of a fish field a disinfecting product comprising an aqueous solution of peracetic acid and hydrogen peroxide, whereby peracetic acid comprises a percentage by weight ranging between 2% and 15% of the disinfecting product, hydrogen peroxide comprises a percentage by weight ranging between 4% and 21%, and the dosage range of the disinfecting product is between 15 and 40 ppm in the water of the fish field, and wherein the edible fish are not harmed by the disinfecting product.

7. A method for destroying microorganisms that affect edible fish fauna, such fauna not being mussels and that are present in an artificially formed field for growing edible fish, said method including the step of pouring into the water of a fish field a disinfecting product comprising an aqueous solution of peracetic acid and hydrogen peroxide, whereby peracetic acid comprises a percentage by weight ranging between 2% and 15% of the disinfecting product, hydrogen peroxide comprises a percentage by weight ranging between 4% and 21% of the disinfecting product, and the dosage range of the disinfecting product is between 15 and 40 ppm in the water of the fish field, and wherein the edible fish are not harmed by the disinfecting product.

8. A method for destroying microorganisms that affect edible fish fauna and that are present in an artificially formed field for growing edible fish, said method including the step of pouring into the water of a fish field a disinfecting product comprising an aqueous solution of peracetic acid and hydrogen peroxide, whereby peracetic acid comprises a percentage by weight of about 5% of the disinfecting product, hydrogen peroxide comprises a percentage by weight of about 20% of the disinfecting product, and the dosage range of the disinfecting product is between 15 and 40 ppm in the water of the fish field, and wherein the edible fish are not harmed by the disinfecting product.

* * * * *